United States Patent
Shinada

(10) Patent No.: US 10,545,118 B2
(45) Date of Patent: Jan. 28, 2020

(54) DIELECTRIC BARRIER DISCHARGE IONIZATION DETECTOR

(71) Applicant: Shimadzu Corporation, Kyoto (JP)

(72) Inventor: Kei Shinada, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/698,351

(22) Filed: Sep. 7, 2017

(65) Prior Publication Data

US 2018/0067083 A1    Mar. 8, 2018

(30) Foreign Application Priority Data

Sep. 8, 2016 (JP) ................................ 2016-175505

(51) Int. Cl.
| | | |
|---|---|---|
| *G01N 27/70* | (2006.01) | |
| *G01N 27/60* | (2006.01) | |
| *G01N 30/64* | (2006.01) | |
| *G01N 33/00* | (2006.01) | |
| *H05H 1/00* | (2006.01) | |

(Continued)

(52) U.S. Cl.
CPC ............. *G01N 27/70* (2013.01); *G01N 27/60* (2013.01); *G01N 30/64* (2013.01); *G01N 33/0027* (2013.01); *H05H 1/0006* (2013.01); *G01N 2030/025* (2013.01); *G01R 19/0061* (2013.01)

(58) Field of Classification Search
CPC .... G01N 27/68; G01N 30/64; G01N 33/0027; G01N 27/66; G01N 2030/025; H05H 1/2406; H05H 1/0081; H05H 1/0006; H05H 2001/2443; G01R 19/0061
See application file for complete search history.

(56) References Cited

U.S. PATENT DOCUMENTS

| | | |
|---|---|---|
| 4,282,521 A | 8/1981 | Lieberman |
| 6,489,585 B1 | 12/2002 | Nakamura et al. |
| 2009/0236042 A1 | 9/2009 | Wada et al. |

(Continued)

FOREIGN PATENT DOCUMENTS

| | | |
|---|---|---|
| CN | 102368060 A | 3/2012 |
| CN | 102866224 A | 1/2013 |

(Continued)

OTHER PUBLICATIONS

Kogelschatz, Dielectric-barrier Discharges: Their History, Discharge Physics, and Industrial Applications, Plasma Chemistry and Plasma Processing, vol. 23, No. 1, Mar. 2003.*

(Continued)

*Primary Examiner* — Daniel R Miller
(74) *Attorney, Agent, or Firm* — Maier & Maier, PLLC

(57) ABSTRACT

A dielectric barrier discharge ionization detector (BID) capable of achieving a high level of signal-to-noise ratio in a stable manner is provided. In a BID having a high-voltage electrode, upstream-side ground electrode and downstream-side ground electrode circumferentially formed on the outer circumferential surface of a cylindrical dielectric tube, a heater for heating the cylindrical dielectric tube or tube-line tip member attached to the upper end of the same tube is provided. Increasing the temperature of the cylindrical dielectric tube by this heater improves the stability of the electric discharge, whereby the amount of noise is reduced and a high level of signal-to-noise is achieved.

2 Claims, 3 Drawing Sheets

(51) Int. Cl.
*G01N 30/02* (2006.01)
*G01R 19/00* (2006.01)

(56) References Cited

U.S. PATENT DOCUMENTS

| | | | |
|---|---|---|---|
| 2010/0320916 A1* | 12/2010 | Yagi | B01J 19/088 |
| | | | 315/111.21 |
| 2011/0168881 A1* | 7/2011 | Sturgeon | H01J 49/142 |
| | | | 250/282 |
| 2011/0260732 A1 | 10/2011 | Shinada et al. | |
| 2011/0316552 A1* | 12/2011 | Shinada | G01N 27/70 |
| | | | 324/464 |
| 2013/0154658 A1 | 6/2013 | Shinada et al. | |
| 2014/0145724 A1 | 5/2014 | Shinada et al. | |
| 2015/0369777 A1 | 12/2015 | Shinada et al. | |
| 2017/0292904 A1 | 10/2017 | Xing et al. | |
| 2018/0067079 A1 | 3/2018 | Shinada et al. | |
| 2018/0067080 A1 | 3/2018 | Shinada et al. | |
| 2018/0067081 A1 | 3/2018 | Shinada et al. | |
| 2018/0067082 A1 | 3/2018 | Shinada et al. | |

FOREIGN PATENT DOCUMENTS

| | | | |
|---|---|---|---|
| JP | 2002260590 A | 9/2002 | |
| JP | 2005247647 A | 9/2005 | |
| JP | 2006128037 A | 5/2006 | |
| JP | 2007029896 A | 2/2007 | |
| JP | 2010-060354 A | 3/2010 | |
| JP | 2013-125022 A | 6/2013 | |
| JP | 2014167488 A | 9/2014 | |
| JP | 20141657488 A | 9/2014 | |
| WO | 2009091065 A1 | 7/2009 | |
| WO | 2012/169419 A1 | 12/2012 | |

OTHER PUBLICATIONS

Shinada et al., "Development of New Ionization Detector for Gas Chromatography by Applying Dielectric Barrier Discharge", Shimadzu Hyouron (Shimadzu Review), vol. 69, Nos. 3/4, Mar. 29, 2013, pp. 255-263.

Office Action dated Nov. 1, 2018 in corresponding U.S. Appl. No. 15/698,312; 12 pages.

Notice of Allowance dated Oct. 17, 2018 in corresponding U.S. Appl. No. 15/698,391; 13 pages.

Notice of Allowance dated Jun. 14, 2019 in corresponding U.S. Appl. No. 15/698,312; 19 pages.

Office Action dated Jun. 14, 2019 in corresponding U.S. Appl. No. 15/698,331; 20 pages.

Notice of Allowance dated Jun. 25, 2019 in corresponding U.S. Appl. No. 15/698,368; 13 pages.

Office Action dated May 28, 2019, in corresponding Chinese Application No. 201710798481.9 including partial machine-generated English-language translation; 9 pages.

Japanese Office Action dated Nov. 12, 2019, in corresponding Japanese Patent Application No. 2016-175502 (8 pages including machine-generated English translation).

Japanese Office Action dated Nov. 12, 2019, in corresponding Japanese Patent Application No. 2016-175503 (6 pages including machine-generated English translation.).

Japanese Office Action dated Nov. 12, 2019, in corresponding Japanese Patent Application No. 2016-175505 (6 pages including machine-generated English translation.).

Office Action dated Nov. 21, 2019, in corresponding U.S. Appl. No. 15/698,331; 13 pages.

* cited by examiner

DIELECTRIC BARRIER DISCHARGE IONIZATION DETECTOR

TECHNICAL FIELD

The present invention relates to a dielectric barrier discharge ionization detector which is primarily suitable as a detector for a gas chromatograph (GC).

BACKGROUND ART

In recent years, dielectric barrier discharge ionization detectors (which are hereinafter abbreviated as the "BIDs") employing the ionization by dielectric barrier discharge plasma have been put to practical use as a new type of detector for GC (for example, see Patent Literatures 1 and 2 as well as Non Patent Literature 1).

BIDs described in the aforementioned documents are roughly composed of a discharging section and a charge-collecting section which is located below the discharging section. In the discharging section, a low-frequency AC high voltage is applied to a plurality of plasma generation electrodes circumferentially formed on the outer wall of a tube made of a dielectric material, such as quartz glass ("dielectric tube"), to ionize an inert gas (plasma generation gas) supplied into the tube line of the dielectric tube and thereby form atmospheric-pressure non-equilibrium plasma. Due to the effects of the light emitted from this plasma (vacuum ultraviolet light), excited species and other elements, the sample components in a sample gas introduced into the charge-collecting section are ionized. The resulting ions are collected through a collecting electrode provided in the charge-collecting section, to generate detection signals corresponding to the amount of ions, i.e. the amount of sample components.

CITATION LIST

Patent Literature

Patent Literature 1: JP 2010-60354 A
Patent Literature 2: WO 2012/169419 A
Patent Literature 3: JP 2013-125022 A

Non Patent Literature

Non Patent Literature 1: Shinada and four other authors, "Development of New Ionization Detector for Gas Chromatography by Applying Dielectric Barrier Discharge", *Shimadzu Hyouron* (*Shimadzu Review*), Vol. 69, Nos. 3/4, Mar. 29, 2013

SUMMARY OF INVENTION

Technical Problem

In the BID having the plasma generation electrodes circumferentially formed on the outer wall of the dielectric tube in the previously described manner, the wall surface of the cylindrical dielectric tube is present between the plasma generation electrodes and the passage of the plasma generation gas. Therefore, this dielectric wall itself functions as a dielectric coating layer which covers the surface of each plasma generation electrode, enabling the dielectric barrier discharge to occur. In the dielectric barrier discharge, the dielectric layer which covers the surface of the plasma generation electrodes prevents an emission of thermions or secondary electrons from the surface of the metallic electrodes. Furthermore, since the plasma generated by the dielectric barrier discharge is a non-equilibrium plasma with low-temperature neutral gas, various factors which cause a fluctuation of the plasma are suppressed, such as a temperature fluctuation in the discharging section. As a result, the BID can maintain plasma in a stable form and thereby achieve a higher level of signal-to-noise (SN) ratio than the flame ionization detector (FID), which is the most commonly used type of detector for GC.

However, in the previously described conventional BID, the amount of noise may increase depending on the measurement conditions. Accordingly, there is still room to improve the SN ratio.

The present invention has been developed in view of such a point. Its objective is to provide a BID capable of achieving a high level of SN ratio in a stable manner.

Solution to Problem

To solve the previously described problem, the present inventor has conducted exhaustive research and consequently discovered that the SN ratio of the BID can be improved by heating the discharging section. Thus, the present invention has been completed.

That is to say, the dielectric barrier discharge ionization detector according to the present invention developed for solving the previously described problem includes:

a) a first gas passage provided with a dielectric tube through which a plasma generation gas is passed;

b) a plasma generator for generating a dielectric barrier discharge within the first gas passage by a low-frequency AC electric field and for generating plasma from the plasma generation gas by the discharge;

c) a second gas passage connected to a downstream portion of the first gas passage;

d) a sample gas introducer for introducing a sample gas into the second gas passage;

e) a current detector for detecting an ion current formed by a sample component in the sample gas ionized by an effect of the plasma within the second gas passage; and f) a heating device provided for the first gas passage.

In the present invention, the first gas passage and the plasma generator correspond to the discharging section mentioned earlier, while the second gas passage, sample gas introducer and current detector correspond to the charge-collecting section mentioned earlier. The heating device may be provided at the dielectric tube and/or other members constituting the first gas passage, such as a member closing the upstream end of the dielectric tube ("tube-line tip member", which will be described later).

In the dielectric barrier discharge ionization detector according to the present invention, the noise in the detection signal obtained from the current detector is reduced by heating the first gas passage with the heating device. Consequently, the SN ratio is improved. A likely reason for this improvement is that heating the first gas passage increases the temperature of the inner wall surface of the dielectric tube and allows electric charges on that surface to easily move and be emitted, contributing to the stability of the electric discharge.

It is expected that a higher level of SN-ratio improvement effect can be achieved by setting the temperature of the first gas passage at a higher level. However, when the heat-resistant temperatures of the parts constituting the first gas passage, such as O rings sealing the ends of the dielectric tube or heat insulators, is taken into account, it is reasonable to set the temperature within a range of 80° C.-130° C.

Accordingly, the dielectric barrier discharge ionization detector according to the present invention may preferably further include:

g) a temperature controller for controlling the heating device so as to maintain the first gas passage within a temperature range of 80° C.-130° C.

Conventionally, helium (He) gas or argon (Ar) gas (or He gas containing a trace amount of Ar gas) has typically been used as the plasma generation gas in BIDs. A study performed by the present inventor using a conventional BID to investigate detection signals produced by the BID during the use of those plasma generation gases has revealed that the amount of noise particularly increases when Ar gas (or He gas containing a trace amount of Ar gas) is used, and that this noise can be effectively reduced by heating the first gas passage.

That is to say, in the dielectric barrier discharge ionization detector according to the present invention, the plasma generation gas should preferably be a gas which contains argon.

Advantageous Effects of the Invention

As described to this point, in the dielectric barrier discharge ionization detector according to the present invention, the amount of noise is reduced and a high level of SN ratio is thereby achieved in a stable manner.

DESCRIPTION OF EMBODIMENTS

Modes for carrying out the present invention are hereinafter described using an embodiment.

Embodiment

Figure 1:
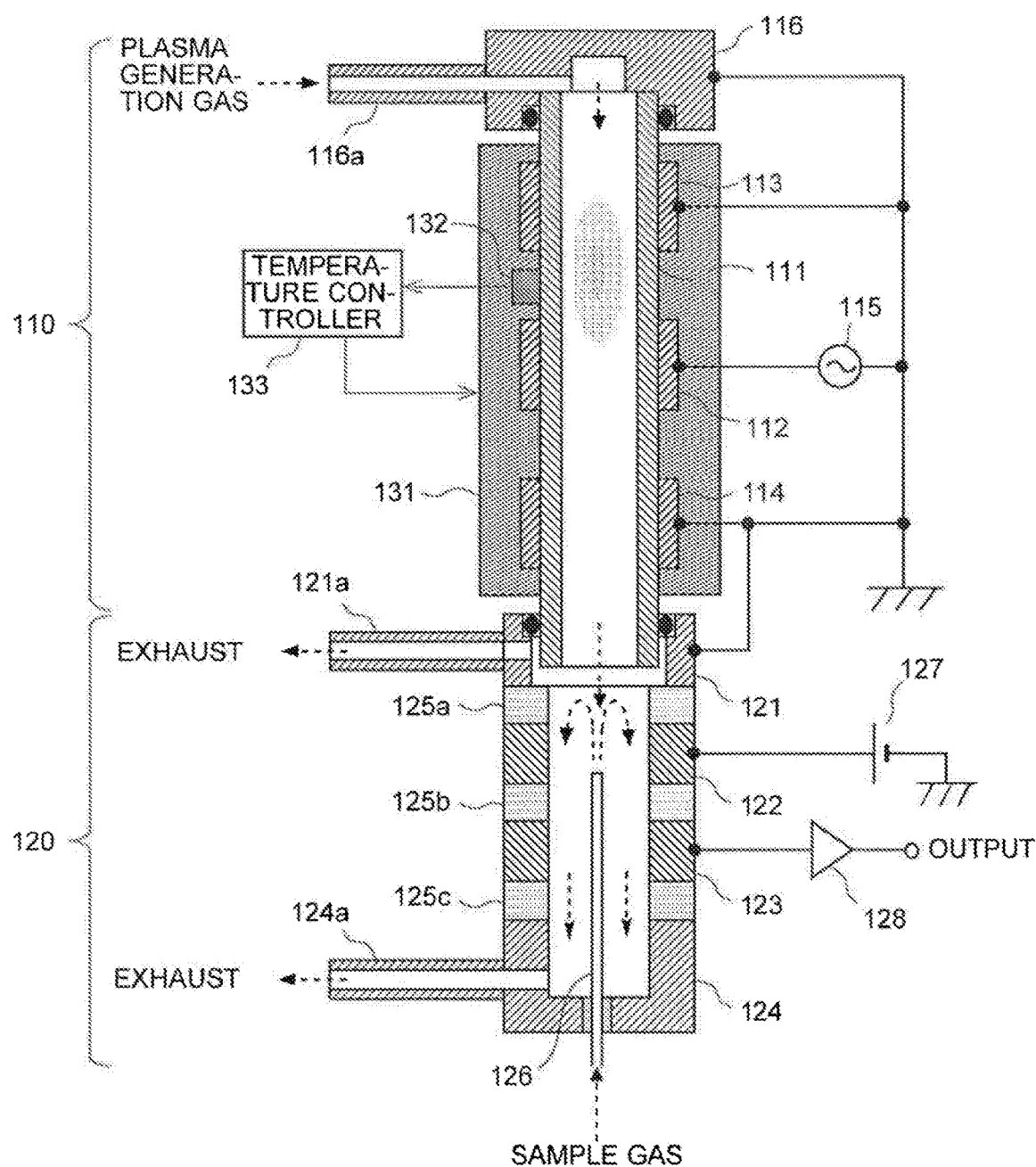
FIG. 1 is a schematic configuration diagram of a BID according to one embodiment of the present invention.

FIG. 1 is a schematic configuration diagram of a BID according to one embodiment of the present invention.

The BID of the present embodiment includes a cylindrical dielectric tube 111 through which a plasma generation gas is passed. In the following description, for convenience of explanation, the vertical direction is defined in such a manner that the upstream side in the flow direction of the gas (indicated by the downward arrows in FIG. 1) in the cylindrical dielectric tube 111 is called the "upper" side, and the downstream side is called the "lower" side. However, this definition does not limit the direction in which the BID should be used.

On the outer wall surface of the cylindrical dielectric tube 111, three ring-shaped electrodes made of a conductor, such as stainless steel or copper, are arranged along the gas flow direction.

Among the three electrodes, the central electrode 112 has a high AC excitation voltage power source 115 connected, while the two electrodes 113 and 114 located above and below the electrode 112 are both grounded. Hereinafter, the electrodes 112, 113 and 114 are called the "high-voltage electrode", "upstream-side ground electrode" and "downstream-side ground electrode", respectively, and these electrodes are collectively called the "plasma generation electrodes". The high AC excitation voltage power source 115 generates a high AC voltage at a frequency within a range of 1 kHz-100 kHz, more preferably, approximately 5 kHz-30 kHz (low frequency), with an amplitude of approximately 5 kV-10 kV. The AC voltage may have any waveform, such as a sinusoidal, rectangular, triangular or sawtooth wave.

The cylindrical dielectric tube 111 has a tube-line tip member 116 at its upper end, to which a gas supply tube 116a is connected. Through this gas supply tube 116a, a plasma generation gas (which is an inert gas, such as Ar gas, He gas, or He gas containing a trace amount of Ar) doubling as a dilution gas is supplied into the cylindrical dielectric tube 111. Since the wall surface of the cylindrical dielectric tube 111 is present between the plasma generation gas and each of the plasma generation electrodes 112, 113 and 114, the wall surface itself functions as the dielectric coating layer which covers the surfaces of the plasma generation electrodes 112, 113 and 114, enabling a dielectric barrier discharge to occur, as will be described later.

On the downstream side of the cylindrical dielectric tube 111, a connection member 121, bias electrode 122 and collecting electrode 123, all of which are cylindrical bodies having the same inner diameter, are arranged along the gas flow direction, with insulators 125a and 125b made of alumina, PTFE resin or similar material inserted in between. On the downstream side of the collecting electrode 123, a tube-line end member 124 in the form of a cylindrical body with a closed bottom is attached via an insulator 125c. The inner space formed by the connection member 121, bias electrode 122, collecting electrode 123, tube-line end member 124 and insulators 125a, 125b and 125c communicates with the inner space of the cylindrical dielectric tube 111.

In the BID of the present embodiment, the area above the upper end of the connection member 121 is the discharging section 110, while the area below the upper end of the connection member 121 is the charge-collecting section 120. The cylindrical dielectric tube 111 and the tube-line tip member 116 correspond to the "first gas passage" in the present invention, while the passage formed by the connection member 121, bias electrode 122, collecting electrode 123, tube-line end member 124 and insulators 125a, 125b and 125c mentioned earlier corresponds to the "second gas passage" in the present invention.

A bypass exhaust tube 121a for exhausting a portion of the plasma generation gas to the outside is connected to the circumferential surface of the connection member 121. A sample exhaust tube 124a is connected to the circumferential surface of the tube-line end member 124. A thin sample introduction tube 126 is inserted through the bottom of the tube-line end member 124. Through this sample introduction tube 126, a sample gas is supplied into the charge-collecting section 120. The charge-collecting section 120 is heated to a maximum temperature of approximately 450° C. by an external heater (not shown) in order to maintain the sample gas in the gasified state.

The connection member 121 is grounded and functions as a recoil electrode for preventing charged particles in the plasma carried by the gas stream from reaching the collecting electrode 123. The bias electrode 122 is connected to a bias DC power source 127. The collecting electrode 123 is connected to a current amplifier 128.

The operation for detecting a sample component contained in a sample gas in the present BID is hereinafter schematically described. As indicated by the rightward arrow in FIG. 1, a plasma generation gas doubling as a dilution gas is supplied through the gas supply tube 116a into the cylindrical dielectric tube 111. The plasma generation gas flows downward through the cylindrical dielectric tube 111, a portion of which is exhausted through the bypass exhaust tube 121a to the outside, while the remaining portion serving as the dilution gas flows downward through the charge-collecting section 120, to be exhausted through the sample exhaust tube 124a to the outside. Meanwhile, the sample gas containing the sample component is supplied through the sample introduction tube 126 and ejected from the sample-gas ejection port at the end of the same tube into the charge-collecting section 120. Although the direction in which the sample gas is ejected from the sample-gas ejection port is opposite to the flow direction of the dilution gas, the sample gas is immediately pushed backward, being merged with the dilution gas and flowing downward, as indicated by the arrows in FIG. 1.

As noted earlier, while the plasma generation gas is flowing through the cylindrical dielectric tube 111, the high AC excitation voltage power source 115 applies a high AC voltage between the high-voltage electrode 112 and the upstream-side ground electrode 113 as well as between the high-voltage electrode 112 and the downstream-side ground electrode 114. As a result, a dielectric barrier discharge occurs within the cylindrical dielectric tube 111, whereby the plasma generation gas is ionized and a cloud of plasma (atmospheric-pressure non-equilibrium plasma) is generated. The excitation light emitted from the atmospheric-pressure non-equilibrium plasma travels through the discharging section 110 and the charge-collecting section 120 to the region where the sample gas is present, and ionizes the sample component in the sample gas. The thereby generated ions move toward the collecting electrode 123 due to the effect of the electric field created by the DC voltage applied to the bias electrode 122. Upon reaching the collecting electrode 123, the ions give electrons to or receive electrons from the same electrode. Consequently, an ion current corresponding to the amount of ions generated from the sample component by the action of the excitation light, i.e. an ion current corresponding to the amount of sample component, is fed to the current amplifier 128. The current amplifier 128 amplifies this current and produces a detection signal. In this manner, the BID according to the present embodiment produces a detection signal corresponding to the amount (concentration) of the sample component contained in the sample gas introduced through the sample introduction tube 126.

The basic components of the BID in the present embodiment are the same as those of commonly used BIDs. The previously described basic operation for detection is also similar to that of commonly used BIDs. The structural characteristic of the BID according to the present embodiment exists in that a heater 131 (which corresponds to the "heating device" in the present invention) for heating the discharging section 110 is provided.

Figure 2:
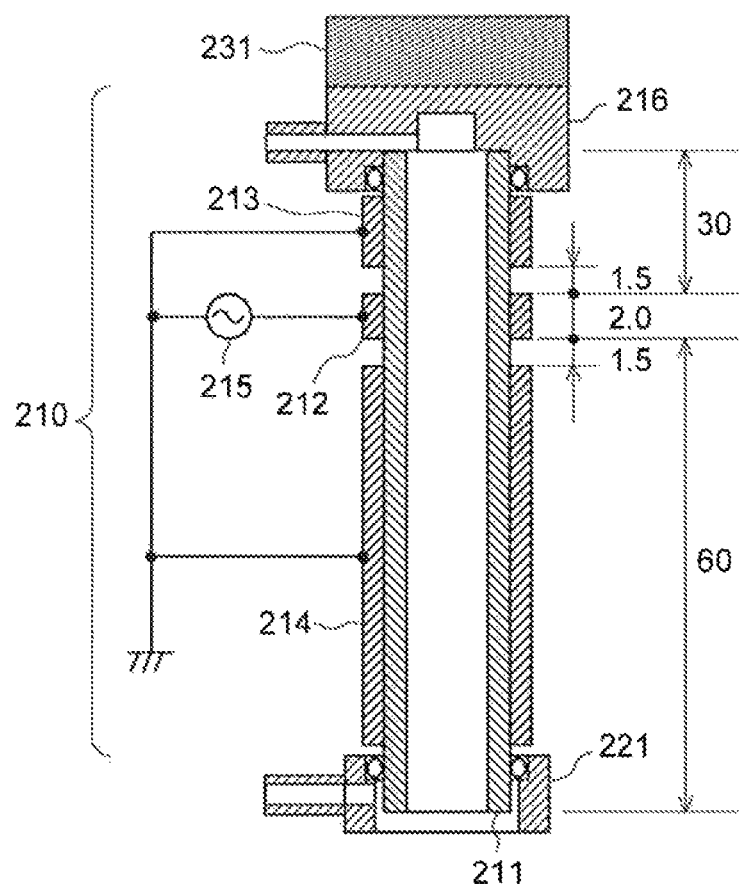
FIG. 2 shows the electrode arrangement of the discharging section in BIDs of a test example and a comparative example.

In the example of FIG. 1, the heater 131 is arranged so as to surround the cylindrical dielectric tube 111, high-voltage electrode 112, upstream-side ground electrode 113 and downstream-side ground electrode 114. However, the position of the heater 131 is not limited to this example; any position is possible as long as the heater can increase the inner temperature of the cylindrical dielectric tube 111. For example, as shown in FIG. 2 (which will be described later), the heater 231 may be provided at the upper portion (or circumferential surface) of the tube-line tip member 216 and heat the cylindrical dielectric tube 11 from the upper end.

Furthermore, a temperature sensor 132 for measuring the temperature of the cylindrical dielectric tube 111 is attached to the outer wall of the cylindrical dielectric tube 111. The temperature sensor 132 and the heater 131 are each connected to a temperature controller 133. The temperature controller 133 controls the heater 131 so that the value of the temperature measured by the temperature sensor 132 is maintained within a range of 80° C.-130° C.

Test Example

Hereinafter described is a test conducted for confirming the effect of the BID according to the present invention. The test was performed using a BID provided with a heater for heating the discharging section (this BID is hereinafter called the "test example") and a BID with no such heater (this BID is hereinafter called the "comparative example"). FIG. 2 shows the electrode arrangement of the discharging section in the test example and the comparative example. It should be noted that the heater 231 shown in the figure was provided only in the test example (the temperature sensor and temperature controller are omitted from the figure). In both of the test and comparative examples, the cylindrical dielectric tube 211 was a quartz tube measuring 4 mm in outer diameter, 2 mm in inner diameter and 92 mm in length. Strips of copper foil were wound on the outer circumferential surface of the cylindrical dielectric tube 211 to form the high-voltage electrode 212, upstream-side ground electrode 213 and downstream-side ground electrode 214.

In the test example, the heating operation with the heater 231 was performed so that the temperature of the outer wall of the cylindrical dielectric tube 211 was maintained at 100° C. In the comparative example, the temperature of the outer wall of the cylindrical dielectric tube 211 was measured. The result was 35° C. and slightly higher than the room temperature. This is due to the fact that the charge-collecting section (120 in FIG. 1) connected to the lower portion of the cylindrical dielectric tube 211 is heated by a heater (not shown), as described earlier.

It should be noted that, in both of the test and comparative examples, the downstream-side ground electrode 214 of the BID was made longer than the upstream-side ground electrode 213. This design was adopted in order to prevent a creeping discharge between the high-voltage electrode 212 and the connection member 221 attached to the lower portion of the cylindrical dielectric tube 211. This design is not directly related to the present invention, and therefore, will not be described in detail.

Using each of those BIDs as the detector for GC, the sensitivity for a solution of a standard sample (dodecane) was measured, with Ar gas (with a degree of purity of 99.9999% or higher) continuously introduced into the cylindrical dielectric tube 211, and the high AC excitation voltage power source 215 energized to apply an AC high voltage having a sinusoidal current waveform at a frequency of approximately 40 kHz with a voltage amplitude of approximately 5 kVp-p. The detection limit was also calculated for each case from the measured noise value. Table 1 below shows the measured results and the calculated results based on the measured results.

TABLE 1

|  | Sensitivity (C/g) | Noise (fA) | Detection Limit (pg/sec) |
|---|---|---|---|
| Test Example | 1.09 | 76 | 0.14 |
| Comparative Example | 1.15 | 236 | 0.41 |

As shown in Table 1, although the sensitivity in the test example was slight lower than in the comparative example, the noise level was significantly reduced. It was confirmed that the detection limit and the SN ratio were consequently improved as compared to the comparative example.

A mode for carrying out the present invention has been described thus far using an embodiment. The present invention is not limited to the previous embodiment and can be appropriately modified within the gist of the present invention.

Figure 3:
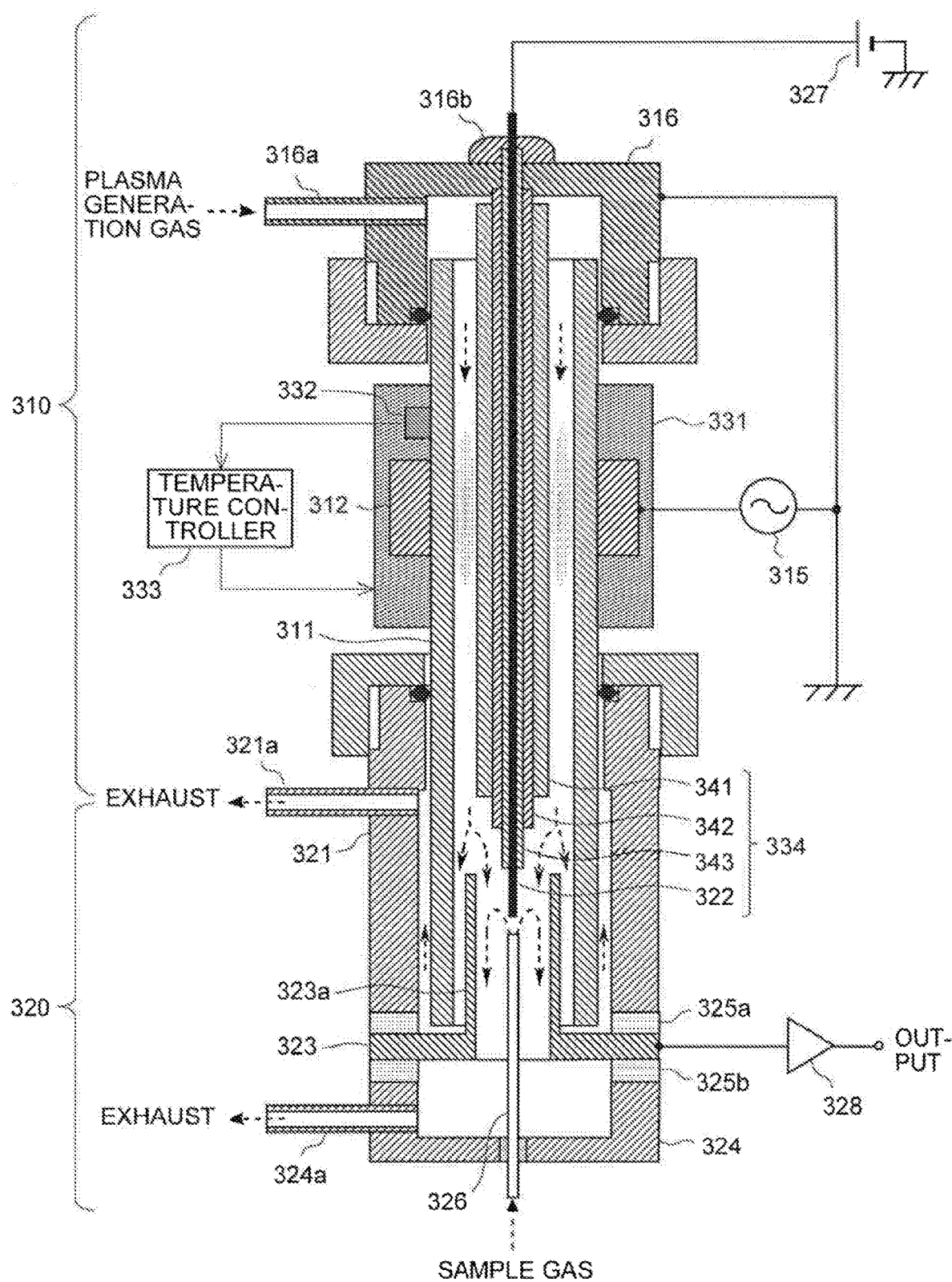
FIG. 3 shows another configuration example of the BID according to the present invention.

For example, the present invention is applicable not only in a BID configured as shown in FIG. 1 having the high-voltage electrode 112, upstream-side ground electrode 113 and downstream-side ground electrode 114 circumferentially formed on the outer circumferential surface of the cylindrical dielectric tube 111; it can also be applied in various configurations of the BID, one example of which is a BID configured as described in Patent Literature 3. FIG. 3 shows an example of the present invention applied in the BID described in Patent Literature 3. In FIG. 3, the components which have corresponding counterparts in FIG. 1 are denoted by numerals whose last two digits are the same as those of their respective counterparts, and their descriptions will be appropriately omitted. In the BID of FIG. 3, a high-voltage electrode 312 is circumferentially formed on the outer circumferential surface of an external dielectric tube 311, and an electrode structure 334 is inserted into this external dielectric tube 311. The electrode structure 334 includes: a metallic tube 342 (which corresponds to a ground electrode) covered with an internal dielectric tube 341 and electrically grounded; an insulator tube 343 contained in the metallic tube 342, and a metallic wire 322 covered with the insulator tube 343. In the BID shown in the figure, a portion which is not covered with the insulator tube 343 ("exposed portion") is formed at the lower end of the metallic wire 322 in the electrode structure 334. The upper end of the metallic wire 322 is connected to a bias DC power source 327. A flanged metallic tube 323 provided in the charge-collecting section 320 is connected to a current amplifier 328. That is to say, in this BID, the exposed portion of the metallic wire 322 functions as the bias electrode, while an upper cylindrical portion 323a of the flanged metallic tube 323 functions as the ion-collecting electrode. Accordingly, the space between the inner wall of the cylindrical portion 323a and the exposed portion of the metallic wire 322 is the effective ion-collecting area. In this BID, the area located upstream of the lower end of the inner dielectric tube 341 corresponds to the discharging section 310, while the area located downstream of that end corresponds to the charge-collecting section 320. The tube-line tip member 316 and the area of the external dielectric tube 311 included in the discharging section 310 correspond to the first gas passage in the present invention, while the area located downstream from the first gas passage to the end of a sample discharge tube 324a in the passage of the plasma generation gas corresponds to the second gas passage. A heater 331 is attached to the first gas passage, surrounding the external dielectric tube 311 and the high-voltage electrode 312. Additionally, a temperature sensor 332 for measuring the surface temperature of the external dielectric tube 311, and a temperature controller 333 which is connected to the heater 331 and the temperature sensor 332, are provided.

REFERENCE SIGNS LIST 110, 210, 310 . . . Discharging Section
111, 211 . . . Cylindrical Dielectric Tube
112, 212, 312 . . . High-Voltage Electrode
113, 213 . . . Upstream-Side Ground Electrode
114, 214 . . . Downstream-Side Ground Electrode
115, 215, 315 . . . High AC Excitation Voltage Power Source
116, 216, 316 . . . Tube-Line Tip Member
116a, 216a, 316a . . . Gas Supply Tube
120, 320 . . . Charge-Collecting Section
121, 221, 321 . . . Connection Member
122 . . . Bias Electrode
123 . . . Collecting Electrode
124, 324 . . . Tube-Line End Member
124a, 324a . . . Sample Exhaust Tube
126, 326 . . . Sample Introduction Tube
127, 327 . . . Bias DC Power Source
128, 328 . . . Current Amplifier
131, 231, 331 . . . Heater
132, 332 . . . Temperature Sensor
133, 333 . . . Temperature Controller
311 . . . External Dielectric Tube
323 . . . Flanged Metallic Tube
323a . . . Cylindrical Portion
334 . . . Electrode Structure
341 . . . Internal Dielectric Tube
342 . . . Metallic Tube
343 . . . Insulator Tube
322 . . . Metallic Wire

The invention claimed is:

1. A dielectric barrier discharge ionization detector, comprising:
    a) a first gas passage provided with a dielectric tube through which a plasma generation gas is passed;
    b) plasma generation electrodes for generating a dielectric barrier discharge within the first gas passage by a low-frequency AC electric field and for generating plasma from the plasma generation gas by the discharge, the plasma electrodes each provided on the dielectric tube;
    c) a second gas passage connected to a downstream portion of the first gas passage;
    d) a sample gas introducer for introducing a sample gas into the second gas passage;
    e) a current detector for detecting an ion current formed by a sample component in the sample gas ionized by an effect of the plasma within the second gas passage;
    f) a heating device arranged for heating the dielectric tube and the plasma generation electrodes, the heating device provided to surround the dielectric tube and the plasma generation electrodes;
    g) a temperature controller for controlling the heating device so as to maintain the dielectric tube within a temperature range of 80° C.-130° C.

2. The dielectric barrier discharge ionization detector according to claim 1, wherein the plasma generation gas is a gas which contains argon.

* * * * *